United States Patent [19]

Adam et al.

[11] Patent Number: 4,812,052
[45] Date of Patent: Mar. 14, 1989

[54] APPARATUS FOR CREEP ENDURANCE TESTING STRUCTURAL COMPONENTS

[75] Inventors: Peter Adam, Dachau; Thomas Sedlmair, Biberbach; Manfred Podlech, Hebertshausen, all of Fed. Rep. of Germany

[73] Assignee: MTU Motoren-und Turbinen-Union Muenchen GmbH, Munich, Fed. Rep. of Germany

[21] Appl. No.: 94,828

[22] Filed: Sep. 9, 1987

[30] Foreign Application Priority Data

Sep. 12, 1986 [DE] Fed. Rep. of Germany ....... 3631153

[51] Int. Cl.⁴ .............................................. G01N 3/18
[52] U.S. Cl. ............... 374/50; 33/DIG. 13; 73/760; 219/10.491
[58] Field of Search ............. 219/10.491, 10.57; 374/50, 57, 45, 46; 33/DIG. 13; 73/760, 763, 805

[56] References Cited

U.S. PATENT DOCUMENTS

| | | | |
|---|---|---|---|
| 1,725,465 | 8/1929 | Manson | 219/10.491 X |
| 1,997,741 | 4/1935 | Northrup | 219/10.491 |
| 3,026,709 | 3/1962 | Gautier et al. | 374/50 |
| 4,608,473 | 8/1986 | Paek et al. | 219/10.491 |
| 4,618,267 | 10/1986 | Burke et al. | 374/46 |

*Primary Examiner*—Roy N. Envall, Jr.
*Attorney, Agent, or Firm*—W. G. Fasse; D. H. Kane, Jr.

[57] ABSTRACT

Structural components, especially components having complicated configurations, are endurance tested for their creep resistance or strength in a removable massive metal testing block which encloses the component being tested in the manner of a mold. The mold type testing block is made of a high heat resistant metal acting as a susceptor in an induction heating system in which the testing block is surrounded by an induction heating coil. In this system the component being tested can be heated to high, highly constant temperatures which provides a substantial improvement in the creep testing results and reduces the cost of testing.

8 Claims, 4 Drawing Sheets

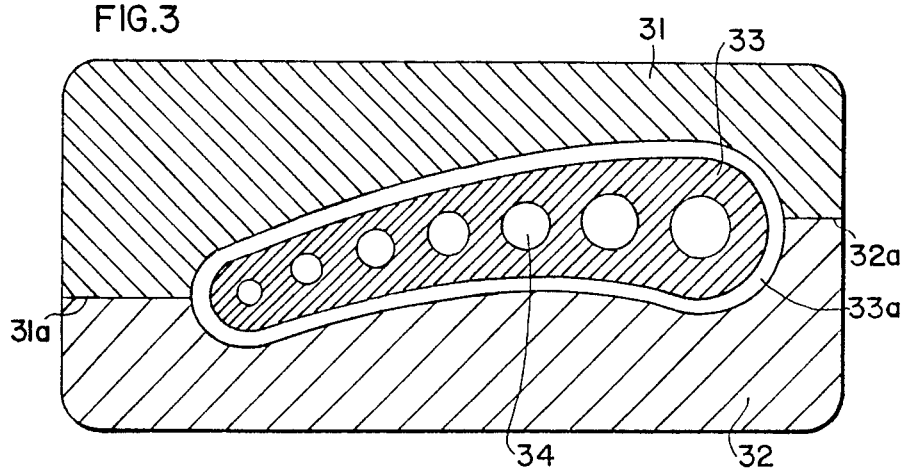
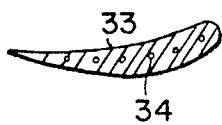
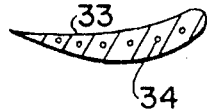
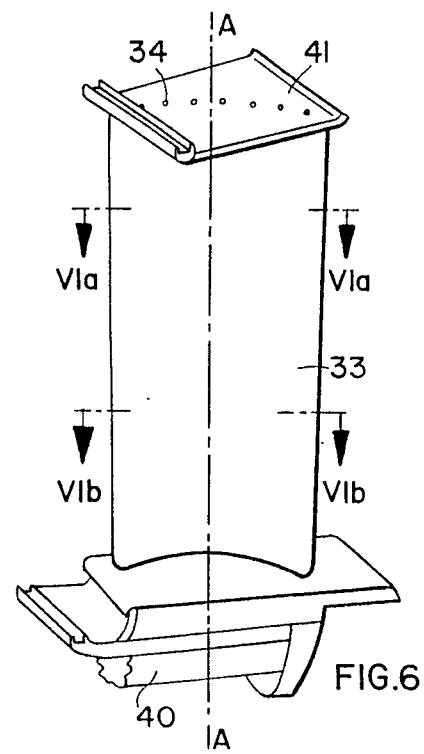

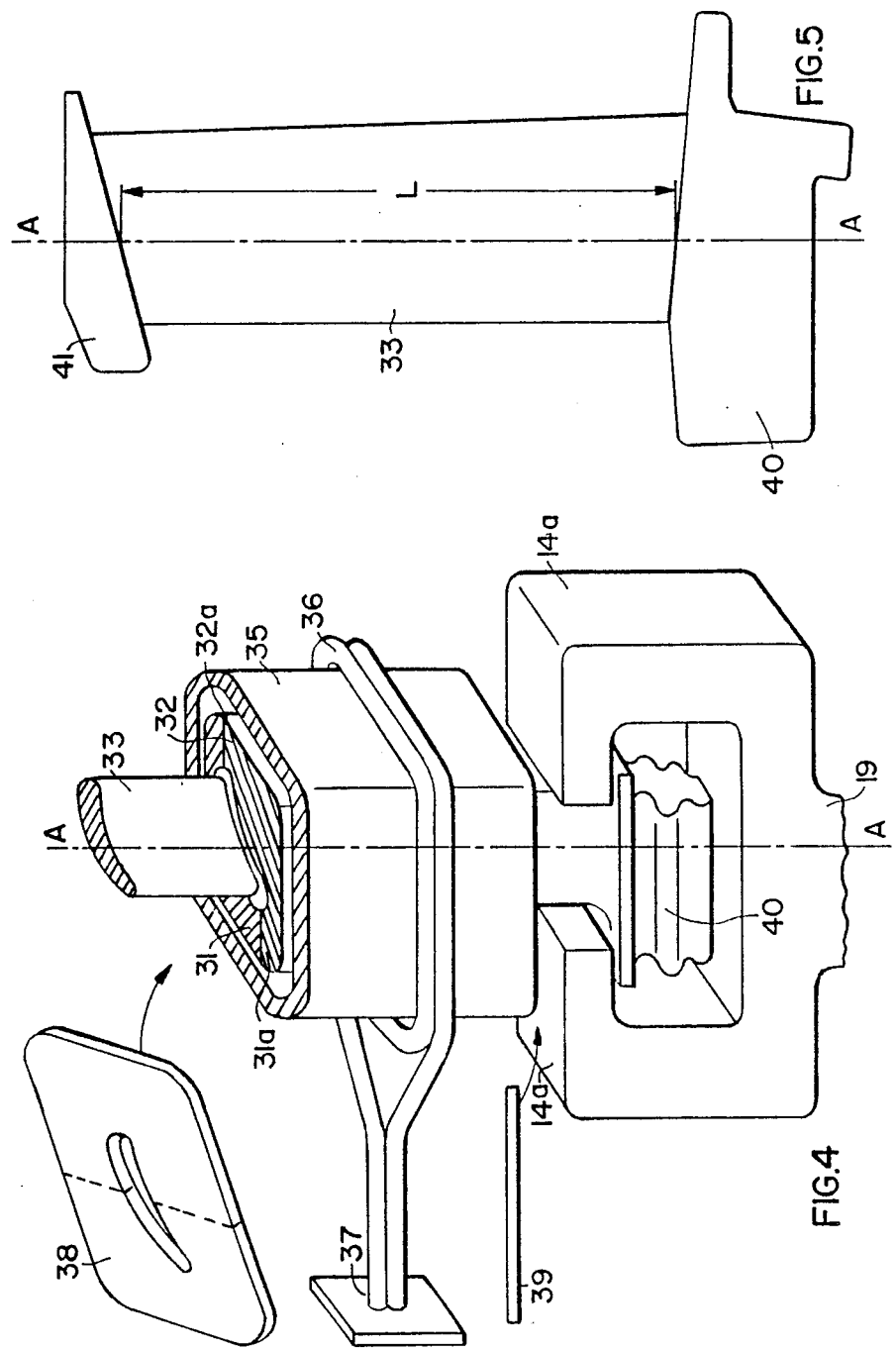

APPARATUS FOR CREEP ENDURANCE TESTING STRUCTURAL COMPONENTS

FIELD OF THE INVENTION

The invention relates to an apparatus for creep endurance testing of structural components, especially components which have a complicated configuration and which must be tested at high temperatures.

DESCRIPTION OF THE PRIOR ART

As a general rule, such components, especially in the field of mechanical enginnering, must pass certain testing so that a prediction can be made regarding the reliability of the component in actual use. These tests are generally designed to provide information regarding the useful life of a component or regarding the planning of maintenance and retesting intervals to make sure that structural failures are excluded with certainty between maintenance and retesting times. The information obtained by such tests is of special interest in connection with structural components which during their use are exposed to high stress and respective wear and tear, particularly resulting from combined load conditions caused by a nonstationary dynamic operation and in a stationary operation as is the case, for example in flow dynamic engines such as turbo-engines. Such tests must yield results permitting a determined statistical prognosis regarding the expected behaviors of the structural component either for a predetermined time duration, or for a predicted useful life of the component. The latter prediction is supposed to indicate when the component will be destroyed, for example, by breaking or similarly severe damage.

In order to obtain the above information so-called time endurance tests are performed for obtaining creep time endurance data. These tests are conventionally tension stress tests performed on heated samples in so-called universal testing machines, whereby the strength against creeping may also be ascertained in accordance with German Industrial Standards DIN No. 50118 which describes standardized testing procedures for performing creep tests under tensile stress and elevated testing temperatures. However, in the present context similar or additional tests are intended to be performed on so-called universal testing machines.

Conventional testing devices comprise a base supporting a motor driven spindle connected to a tension applying device made of steel. The component to be tested also referred to as the test sample, is mounted in an oven and the oven in turn is arranged in a frame in such a way that the mounting or suspension for the test sample can be subjected to a load such as a counterweight. In order to achieve a heat expansion of the test sample during the testing, the oven is heated in a conventional manner, usually by means of an electrical pipe type heater embedded in the walls of the oven. The heater transmits its heat to the test sample by heat radiation. Conventional ovens contain an atmosphere either of air or a protective gas or a reduced pressure. The heat transmissions from the heat source to the test sample must pass through the air or protective gas or the reduced pressure volume. Normally, a material sample is tested rather than actual components.

It has been found that applying the above described testing or rather using the above described testing apparatus for structural components, especially finished structural components having a complicated configuration, is inadequate to provide the informations necessary for making the required prognosis. This applies especially to structural components which are subjected to a cooling and/or solidification as part of their production. In these instances the prior art devices and prior art testing procedures are not sufficiently representative for obtaining the required information.

Structural components, especially case components having a high strength and especially a high creeping strength, depend for these characteristics on the material structure or texture. This material structure or texture in turn depends on the type of the solidification of the metallic materials. For example, the creeping strength depends on the grain size, the grain structure, and on the grain boundaries. Other factors influencing the material strength, especially the creeping strength, involve the heat dissipation during the solidification, and on the solidification cycle or temperature time program as well as on the materials which surround the cast component such as the material of which the mold or mold shells are made.

Another disadvantage of prior art testing devices resides in the fact that it is not possible to obtain exactly defined temperature conditions throughout the volume and profile of the test sample. For example, it has been found that in endurance tests of flow dynamic engine blades certain portions of the blades, especially the blade cores, are exposed to an excessive heating so that the obtained test results do not apply without limitations. The prior art has tried to remove or avoid this problem by using hot gas corrosion testing facilities which make the stresses to which the blades are exposed in operation, quite well visible. However, employing such testing facilities involves an extraordinarily high effort and expenditure for the equipment and additionally requires high operational costs.

OBJECTS OF THE INVENTION

In view of the foregoing it is the aim of the invention to achieve the following objects singly or in combination:

to provide a simple, yet rugged testing apparatus for the purposes outlined above which nevertheless provides precise test results which permit making the above mentioned prognosis;

to provide a testing apparatus for performing a creep endurance test in accordance with a given time temperature program providing prognosis supporting test results for a certain operational time duration or for a statistically useful life of the tested components;

to heat the test sample throughout its volume as uniformly as possible, at least in that zone of the test sample that in actual use will be exposed to the highest thermal loads; and to apply to the uniformly heated test sample a reproducible tension load simultaneously with the thermal load.

SUMMARY OF THE INVENTION

A testing apparatus according to the invention achieves the above objectives by the following features. A mold type member having an inner surface conforming to the configuration of the test sample is arranged to enclose the test sample. The mold type member is made of a highly heat resistant metal for forming a susceptor. Preferably, the mold type member is a solid block which is surrounded by an induction heating coil.

The above features enable a testing procedure which can exactly control the timing and the thermal effects of the heating elements, thereby adapting these effects in the desired manner to the type of test sample. In other words, the testing sequence can be performed with a highly constant temperature over time and throughout the volume of the test sample, or at least throughout the volume of the test sample that requires a uniform heating. Simultaneously, the arrangement of the heating element as claimed herein is such that a mechanically stable and anytime repeatable tension load can be applied to the test sample without any trouble.

Further advantageous features of the invention are defined in the claimes.

BRIEF DESCRIPTION OF THE DRAWINGS

In order that the invention may be clearly understood, it will now be described, by way of example, with reference to the accompanying drawings, wherein:

FIG. 3 is a sectional view through a mold type member according to the invention, and through a test sample, such as a turbine blade, held in the mold type member;

FIG. 4 is a perspective view, especially through the heating oven and through a test sample mounting member of the present apparatus;

FIG. 5 is a front or side view of a test sample such as a turbine blade;

FIG. 6 shows the test sample of FIG. 5 in a perspective view;

FIG. 6a is a sectional view along section line VIa—VIa in FIG. 6; and

FIG. 6b is a sectional view along section line VIb—VIb in FIG. 6.

DETAILED DESCRIPTION OF PREFERRED EXAMPLE EMBODIMENTS AND OF THE BEST MODE OF THE INVENTION

Figure 1:
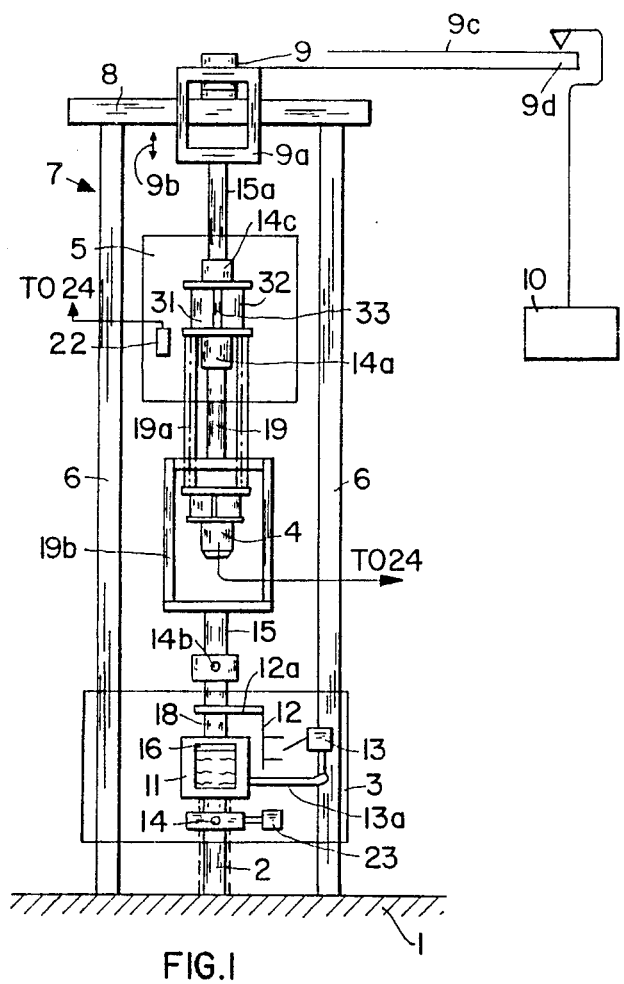
FIG. 1 is a front view of the testing apparatus according to the invention.
Figure 2:
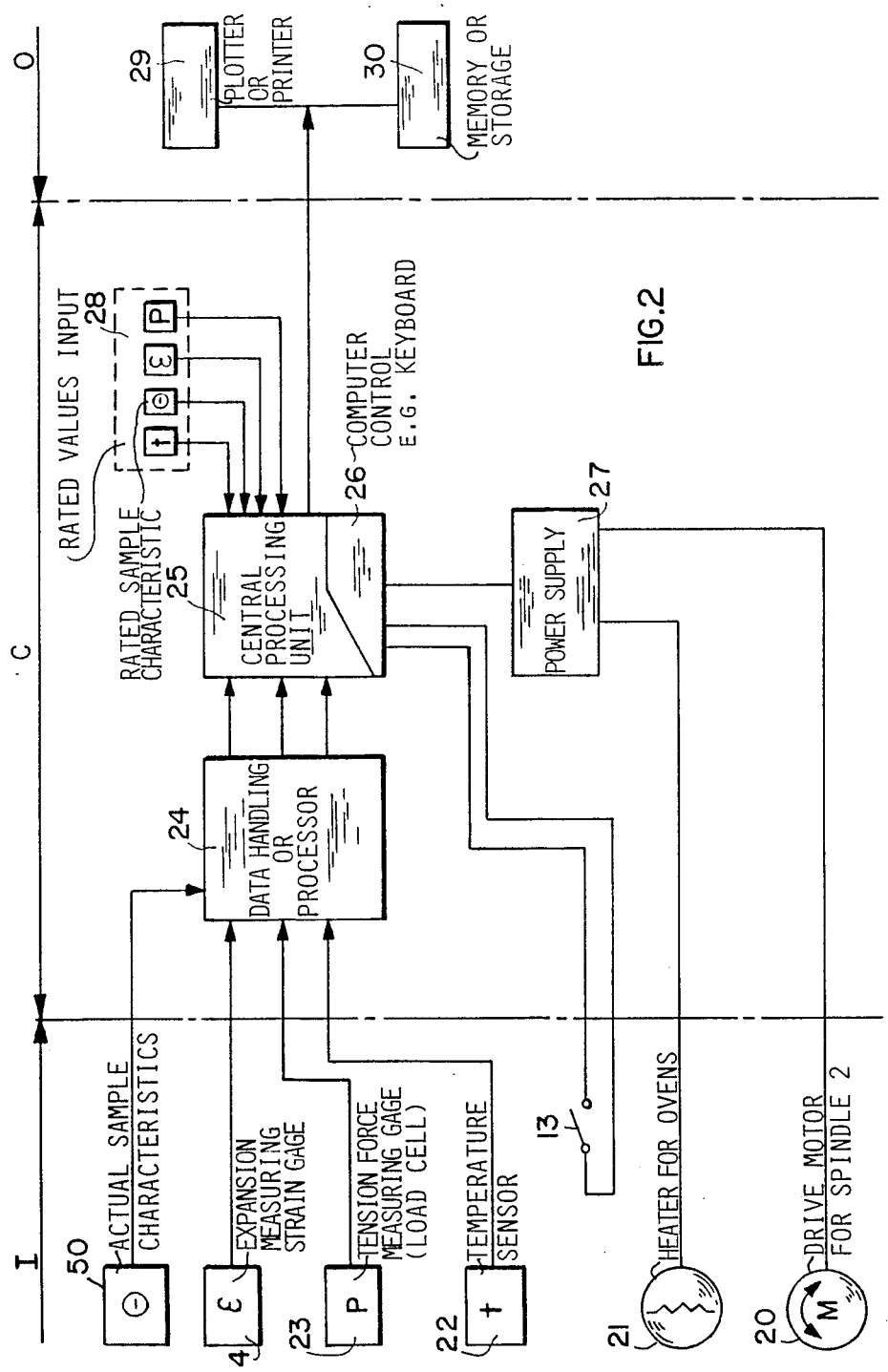
FIG. 2 is a block diagram of the sensing, control, and evaluating sections of the present apparatus.

FIG. 1 shows a testing apparatus equipped according to the invention comprising a machine bed 1 carrying a motor 20, see FIG. 2, for driving a spindle 2 or any equivalent device for properly locating a test sample 33 in the apparatus. A conventional expansion compensating unit 3 is operatively interposed between the spindle 2 and the test sample 33. The compensating unit 3 performs several functions, namely a switching function with a position responsive switch 13, a damping function with a fluid cylinder 11, and a hysteresis compensating function with a sensor 12 which operates the switch 13. A measuring sensor 4, such as a strain gage or the like, is located in a frame member 19b connected to the test sample 33 through a quartz rod 19 which in turn is connected to a test sample holding claw 14a shown in more detail in FIG. 4. The strain sensor 4 is connected to the test sample 33 through a separate frame 19a. The test sample 33 itself is located in a space formed by two metallic susceptors 31 and 32 as will be described in more detail below with reference to FIG. 4. The strain gage mounting frame 19a is movable independently of the frame member 19b.

Referring further to FIG. 1, a coupling 14 connects the tension force measuring gage, such as a load cell 23, to the spindle. The output of the load cell 23 is supplied to a central computer section C shown in FIG. 2. The spindle 2 is, as mentioned, connected to a damping piston cylinder device 11, the piston 16 of which is connected through a rod 18 to a further coupling 14b coupled by a rod 15 to the frame 19b. The frame 19b in turn is connected through the quartz rod 19 to the sample holding claw 14a. The upper end of the sample 33 is connected through a further coupling 14c and a further rod 15a to a tension applying frame 9a which is slidably movable in the cross-beam 8 of the frame structure 7 formed by a number of columns 6. The upper portion of the frame 9a is connected to one end 9 of the lever 9c pivoted in a fulcrum not shown. Actually, the lever 9c extends into and behind the plane of the sheet of the drawing, but is shown rotated 90° into the plane of the drawing to indicate that a weight 10 is applied to the outer end 9d of the lever 9c. The length of the lever end 9 between its connection to the frame member 9a and the fulcrum, to the length of the lever 9c between the fulcrum and the end 9d is in the order of 1:20. As mentioned, the just described components are all operatively supported in the frame structure 7 and the up or down movement of the frame 9a is indicated by the arrow 9b. An oven 5 to be described below with reference to FIG. 4 heats the test sample 33 inside the susceptors 31 and 32 forming a mold type member in an induction heating device inside the oven 5.

The entire arrangement is such, that as a result of the heating of the test sample 33 the latter is enabled to expand and such expansion is sensed by the strain sensor 4 located outside the oven 5. A test is performed by heating the sample in the oven 5 to the desired temperature which is measured by a temperature sensor 22, the output signal of which is supplied to the central computing unit C shown in FIG. 2. Simultaneously, a tension load is applied through the weight 10 and the levers 9, 9c to the test sample 33. The respective tension is measured at 23 and the signal is also supplied to the central computing unit C. Additionally, sample specific input values θ may be taken into account, such as the effective length L of the test sample, its cross-sectional area, and any reduced cross-sectional areas of the test sample. The respective input is shown at 50 in FIG. 2.

When a test is completed, the expansion compensating unit 3 is somewhat contracted. Stated differently, the expansion of the test sample 33 has become approximately zero. At this point, the piston 16 of the damping cylinder 11 has been moved into the cylinder 11, whereby any movements of the test sample 33 are damped in a soft elastic manner. Thus, breakage of the mounting assembly components and of the quartz rod 19 is avoided. The use of a quartz rod 19 and frame members 19a also of quartz is desirable since they are exposed to the heat in the oven 5. The cylinder 11 holds a damping liquid capable of avoiding a sudden downward movement if the test sample 33 should break or rupture. Incidentally, the coupling 14 for the sensor 23 to the spindle 2 may include a conventional clamping bolt shown as a little circle in the coupling 14. The sensor or limit switch 13 is rigidly mounted to the cylinder 11 by a bracket 13a. The hysteresis sensor 12 is connected to the piston rod 18 of the piston 16 by a bracket 12a. The arrangement is such, that the upper portion of the system is movable relative to the lower portion. The extent of such motion corresponds to the expansion or contraction displacement. The piston rod 18 of the piston 16 is hollow so that it may take up any excess fluid when the piston 16 moves downwardly in the cylinder 11. The hysteresis sensor 12 comprises two limit fingers arranged for cooperation with an actuating member of the sensor switch 13. The fingers of the sensor 12 are so spaced from each other that the operation of the switch 13 will provide a measure for the hysteresis displacement.

When the test sample 33 should break, the mounting frame 19b, the quartz rod 19, and the frame 19a as well as the strain sensor 4 move downwardly, whereby the downward motion is damped by the piston 16 in the cylinder 11. Simultaneously, the sensor or limit switch 13 is operated to thereby stop the drive motor of the spindle 2 as well as the heating of the oven 5 by switching off the power supply 27 shown in FIG. 2.

When the test is performed as a function of time, or when it is performed as a function of the expansion of the sample 33, the spindle 2 is initially driven upwardly in response to the numerical control shown in FIG. 2, whereby, after traversing the hysteresis displacements, the limit or sensor switch 13 is also operated to switch-off the spindle 2 and the oven 5. However, in this operational condition, as distinguished from the situation when the test sample broke, there is still an uninterrupted connection to the weight 10 through the lever 9, 9c and the frame 9a. Further, since the oven has been switched off, the temperature drops and as a result, the components inside the oven contract. However, now the hysteresis displacement of the apparatus is available so that the contraction of the test sample 33 can take place, due to the dropping temperature in the oven 5, without causing damage to the test system. Thus, during the contraction phase of a test cycle the entire testing system remains free of stress or tension.

The strain sensor or pick-up 4 is preferably of the type operating in accordance with the principle of an incremental linear measuring system. Stated differently, the displacement to be measured and transmitted by the test sample 33 is effective on the quartz rods 19a. At least one of these rods 19a has etched thereon, for example, by a photo-resist method, a miniature scale which is scanned in a photo-optical manner to produce, without any signal transformation, a binary coded decimal signal which can directly be processed by the central processing unit C shown in FIG. 2. The described system can be switched-off in a fully automatic manner, for example either at the end of a predetermined time period, or at the end of a preadjusted stress expansion.

Referring to FIG. 2, the respective rated values are supplied through an input 28 connected to the central processing unit 25 which may, for example, be a computer model HP-85 manufactured by Hewlitt Packard. The central processing unit 25 includes a computer control such as a keyboard 26 which also controls a power supply 27 for the heater 21 of the oven 5 and for the drive motor 20 of the spindle 2. The output of the central processing unit 25 leads to an output unit O including, for example, a plotter or printer 29 and a memory or information storage device 30. A data handling or processing unit 24 is operatively interposed between the actual value sensors 4, 22, 23, and 50 and the central processing unit 25. The unit 24 may comprise amplifiers, signal shaping circuits, analog-to-digital converting circuits, and so forth. The details of the circuit arrangement of FIG. 2 are not part of the invention.

Similarly, the program, for example a temperature-time program, for the inductive heating of the oven 5, is not part of the invention. Such programs are conventional and stored in the computer sections C so that the operator may run a test simply by punching the respective keys on the computer control 26. Such inputs will also involve the selection of the tension force to be applied to the test sample as well as other mechanical and thermal load values. Further, the sample specific characteristics $\theta$, such as the length L, the cross-sectional area, reductions in the cross-sectional area and other sample characteristics may be taken into account. However, the invention is not concerned with these features of a test procedure which are known as such.

FIG. 3 shows a sectional view horizontally through the test sample 33 in FIG. 1. The mold type mounting member according to the invention comprises two sections 31 and 32 forming a susceptor for an induction heating device to be described below with reference to FIG. 4. The sections 31 and 32 are separated along interface surfaces 31a and 32a so that the test sample 33 may easily be inserted into the mold type member and again removed therefrom. If desired, the inner surface of the sections 31 and 32 are so dimensioned that a gap 33a is formed between the sample 33 and the mold type member. The gap 33a may be filled with a release facilitating agent such as a ceramic paste or the like. The ceramic paste is known as "Stop-Off Withe 110" and may be purchased from the Aerobraze Company. The susceptor sections 31 and 32 are made of a high heat resistant material such as a nickel alloy or a cobalt alloy. Such alloys are well known in the art. The formation of the recesses inside the susceptor or mold member sections 31 and 32 are formed, for example to conform to a fluid flow engine blade forming the test sample 33. The formation of these sections can be accomplished by a conventional machining operation. The outer contour of the sections 31 and 32 will be adapted to the space in the otherwise conventional testing machine.

Incidentally, with regard to FIG. 2 it should be mentioned that the central processing unit 25 performs in addition to its control functions, primarily a comparing function in which the rated input values are compared with the actually measured input values for generating control signals. For example, when a preselected time has expired and that has been measured by the clock generator inside the processing unit 25, the system will be stopped.

Referring to FIG. 4, the above mentioned claw 14a forms a gripper for holding the foot 40 of the test sample 33. The claw itself is connected to the quartz rod 19. The two mold type susceptor sections 31 and 32 are surrounded by a jacket 35 made of a heat insulating material such as a ceramic material, for example $Al_2O_3$. An induction coil 37 is connected to a power source 37 and heats the test sample 33 held in the mold type member which is so dimensioned with regard to the length L of the sample 33, please see FIG. 5, that the required zone of the sample 33 is uniformly or isothermally heated. The insulation jacket 35 may be closed by a heat insulation cover 33 and by a respective bottom similar to the cover 38, but only symbolically shown at 39.

FIG. 4 shows that the tension load and hence the tension stress is introduced in the direction of the longitudinal axis A - A completely separately from the introduction of the thermal load. This feature of the invention has the important advantage that the thermal load introduction and the mechanical load introduction do not interfere with each other. Thus, it is possible to satisfy all the requirements and objectives mentioned above. More specifically, the introduction of the mechanical tension load can be reproduced precisely at any time. Since the introduction of the thermal load is located well above the sample foot 40, the claw 14a remains at a sufficiently low temperature so that the temperature applied to the sample will not affect the performance characteristics of the components for the mechanical load application. Further, the claw 14a can thus be made of less expensive material such as suitable steel. For example, if the test sample 33 is a turbine blade made of a super alloy, the claw 14a could be made of stainless steel. The tension load can be measured below the components, for example, as indicated at 23. A conventional load cell is suitable for this purpose. Although in FIG. 1 the temperature sensor 22 is shown in the oven, in reality it will be placed as close as possible to the surface of the test sample 33. The testing temperature will be maintained constant within a range of about 900° to 1100° C. when turbine blades are being tested. This temperature should be maintained over at least 10% and preferably 80% of the blade length L shown in FIG. 5. Further, the temperature should not deviate in a direction perpendicularly to the longitudinal axis A—A for more than about ±2° C. in the sample 33. This constancy should be maintained throughout the endurance testing duration which may run from as little as ten hours to as many as ten thousand hours.

Although the strain sensor 4 is shown in FIG. 1 outside the oven 5, the strain gage elements themselves are preferably also directly applied to the surface of the test sample, for example in the gap 33a in which the temperature sensors 22 are located.

FIG. 5 shows a side view of a turbine blade 33 with the foot 40 and a head portion 41 and an effective length L. The view of FIG. 6 shows the same blade in a perspective view, whereby the sectional views are to show that the cross-sectional area along the length of the blade may vary. For example, the cross-sectional area closer to the foot 40 is smaller than the cross-sectional area closer to the head 41. These changes in the cross-sectional configuration may also be taken into account in the testing program as mentioned above.

The sample 33 has cooling bores 34 through which cooling air is passed.

Where the test sample does not have a foot, such as shown in connection with a turbine blade, a temporary mounting plate may have to be welded to the sample to make sure that the mechanical load application is separate from the thermal load application.

It has been found that the present mold type susceptor according to the invention applies the heat to the test sample in a very efficient manner so that a relatively small electrical energy can be applied for prolonged periods of time. The heat application is uniform and constant for the required time duration so that the test results needed for the above mentioned prognosis are obtained with a sufficient representative quality in a statistic sense to make predictions for a particular time duration or for a warranted operational life of the particular component. Further, the invention is not limited to test samples in the form of turbine blades. Any type of test samples particularly cast test samples, may be tested in a cost effective manner to ascertain their endurance characteristics, especially their creep resistance.

The invention avoids testing equipment in which hot combustion gases must be applied to the test samples. The present mold type member can also be used in connection with tension stress testing, compression stress testing, ending stress testing, and any combinations of these stresses, including creeping stress. Moreover, the equipment employing the invention may be part of an automatic control system at the end of an assembly line in which all structural components are tested prior to their delivery. Thus, the results of the tests may be delivered together with each component as evidence of a quality control in the form of a testing print-out.

Although the invention has been described with reference to specific example embodiments, it will be appreciated, that it is intended to cover all modifications and equivalents within the scope of the appended claims.

We claim:

1. An apparatus for creep testing a structural component, especially a component having a complicated configuration, comprising a mold type member made of a highly heat resistant metal for forming a heat susceptor, said mold type member having an inner surface so dimensioned that a gap is formed between said inner surface of said mold type member and the surface of said structural component when said structural component is placed in said mold type member conforming substantially to at least a portion of said configuration for enclosing said structural component during testing, means for permitting removal of said structural component from said mold type member, and induction heating coil means surrounding said mold type member for heating said structural component through said mold type member, said apparatus further comprising clamping means arranged for holding a portion of said structural component protruding from said mold type member, and means for applying tension stress to said structural component through said clamping.

2. The apparatus of claim 1, wherein said inner surface of said mold type member corresponds to a negative mold of said structural component to be tested.

3. The apparatus of claim 1, wherein said means for permitting removal of said structural component from said mold type member comprise two or more separable partial shells forming said mold type member.

4. The apparatus of claim 1, wherein said highly heat resistant metal is an alloy based on nickel or cobalt.

5. The apparatus of claim 1, further comprising a jacket of heat insulating material for surrounding said mold type member.

6. The apparatus of claim 1, further comprising a separation paste in said gap.

7. The apparatus of claim 6, wherein said paste is a ceramic paste.

8. The apparatus of claim 1, wherein said inner surface of said mold type member has the configuration of a blade of a flow dynamic engine.

* * * * *